United States Patent [19]
Morley et al.

[11] Patent Number: 5,418,134
[45] Date of Patent: * May 23, 1995

[54] METHOD FOR DIAGNOSIS OF MONOCLONALITY IN LEUKAEMIA AND LYMPHOMA

[75] Inventors: Alexander A. Morley, 12 Barretts Road, Torrens Park, South Australia; Michael J. Brisco, Marino, both of Australia

[73] Assignee: Alexander Alan Morley, Torrens Park, Australia

[*] Notice: The portion of the term of this patent subsequent to Mar. 22, 2011 has been disclaimed.

[21] Appl. No.: 172,415

[22] Filed: Dec. 22, 1993

Related U.S. Application Data

[63] Continuation of Ser. No. 684,889, Jun. 13, 1991, Pat. No. 5,296,351.

[30] Foreign Application Priority Data

Oct. 20, 1988 [AU] Australia .......................... PJ1057/88

[51] Int. Cl.$^6$ .............................................. C12Q 1/68
[52] U.S. Cl. .......................................... 435/6; 435/975
[58] Field of Search ............................ 435/6, 975, 91.2

[56] References Cited

U.S. PATENT DOCUMENTS 4,683,202  7/1987  Mullis ...................................... 435/91

OTHER PUBLICATIONS

Albertini, et al. (1986) "Molecular Characterization of Somatic Gene Mutations Arising In Vivo in humans", *Progress in Clinical and Biological Research* 207, 77–85.
Baer, et al. (1986) "Organization of the T-Cell Receptor α-Chain Gene and Rearrangement in Human T-Cell Leukaemias", *Mol. Biol. Med.* 3, 265–277.
Born, et al. (1985) "Rearrangement of T-Cell Receptor β-Chain Genes During T-Cell Development", *Proc. Natl. Acad. Sci., USA*, 82, 2925–2929.
Chen, et al. (1988) "The Human T-Cell V Gene Locus: Cloning of New Segments and Study of V Rearrangment in Neoplastic T and B Cells", *Blood* 72, 776–783.
Foroni, et al. (1987) "Immunoglobulin Gene Rearrangements in Hairy Cell Leukemia and Other Chronic B Cell Lymphoproliferative Disorders", *Leukemia* 4, 389–392.
Hedrick, et al. (1985) "Rearrangement and Transcription of a T-Cell Receptor β-Chain Gene in Different T-Cell Subsets", *Proc. Natl. Acad. Sci., USA* 82, 531–535.
Kumar, et al. (1986) "Rearrangement of T-Cell Receptor β-Chain Genes in Human Leukaemias", *Molecular Immunology* 23, 1349–1356.
Luzzatto, et al. (1986) "DNA Rearrangements of Cell Lineage Specific Genes in Lymphoproliferative Disorders", *Progress in Hematology* 14, 303–332.
Nakauchi, et al. (1987) "Molecular Evidence that SJL Reticulum Cell Sarcomas are Derived from Pre-B- Cell", *J. Immunol.* 139, 2803–2809.
Rambaldi, et al. (1985) "T Cell Receptor β-Chain Gene Rearrangements in Lympho-proliferative Disorders of Large Granular Lymphocytes/Natural Killer Cells", *J. Exp. Med.* 162, 2156–2162.
Smith, et al. 91986) "DNA Rearrangements in Human B- and T-Cell Malignancies", *Med. Oncol. and Tumor Pharmacother.* 3, 153–157.
Traunecker, et al. 91986) "Rearrangements of T Cell Receptor Loci can be Found Only Rarely in B Lymphoid Cells", *Eur. J. Immunol.* 16, 430–434.
Waldmann (1983) "A Comparison of the Function, Phenotype, and Immunoglobulin Gene Arrangement in Leukemias of Different Human B and T Lymphocyte Subsets", *Progress in Immunology* 5, 1035–1046.
Tonegaua, S. (1983) Nature 302, 575–581.
Yancopoulos, G. D., et al, (1986) Ann. Rev, Immunol. 4, 339–368.
Toyonaga, B. et al., (1987) Ann. Rev. Immunol. 5, 585–620.

*Primary Examiner*—Charles L. Patterson, Jr.
*Attorney, Agent, or Firm*—Scully, Scott, Murphy & Presser

[57] ABSTRACT

The present invention is directed to a method for the detection of leukemia or lymphoma by determining the homogeneity or heterogeneity of the length of immunoglobulin or T-receptor gene segments. The present invention is further directed to a kit that is useful for the detection of leukemia or lymphoma.

33 Claims, No Drawings

METHOD FOR DIAGNOSIS OF MONOCLONALITY IN LEUKAEMIA AND LYMPHOMA

This is a continuation of application Ser. No. 684,889, filed on Jun. 13, 1991 which is now U.S. Pat. No. 5,296,351, corresponding to International Application PCT/AU89/00455 filed on Oct. 20, 1989 and which designated the U.S.

This invention relates to a diagnostic method which may be used in leukaemia and lymphoma for detection of malignancy and determination of its lineage.

Lymphocytes, the cells responsible for immunity, are of two types:

(a) the B-lymphocytes, each of which produces a specific immmunoglobulin molecule which attaches to a particular foreign antigen; and
(b) the T-lymphocytes, each of which has a specific surface receptor which enables the cell to attach to a particular foreign antigen.

Each B-lymphocyte contains a unique immunoglobulin gene which differs moderately in structure from the immunoglobulin gene of all other B-lymphocytes and markedly in structure from the immunoglobulin genes of all other body cells, including T-lymphocytes. Similarly, each T-lymphocyte contains a unique T-receptor gene which differs moderately in structure from the T-receptor gene of all other T-lymphocytes and markedly in structure from the T-receptor gene of all body cells, including B-lymphocytes.

Lymphoid leukaemias and lymphomas are a form of cancer of the lymphocyte tissue. Each leukaemia or lymphoma arises from a single B- or T-lymphocyte which multiples, spreads and eventually results in death unless treated. As all the tumor cells are descended from a single cell, they are all genetically the same and all will contain the same unique gene, a unique immunoglobulin gene if the tumour arose in a B-lymphocyte, or a unique T-receptor gene if the turnout arose in a T-lymphocyte.

Conversely, if a tissue is suspected as being involved by leukaemia or lymphoma the detection of a unique immunoglobulin gene is presumptive evidence of a turnout of B-lymphocytes whereas detection of a unique T-receptor gene is presumptive evidence of a tumour of T-lymphocytes.

The object of the present invention is to determine whether or not leukaemia or lymphoma is present in a tissue sample by determining whether or not a monoclonal B- or T-lymphocyte population is present in the sample. In general terms, the invention does this by focussing on a discrete segment of the immunoglobulin or T-receptor molecule and determining whether all or most of these segments in the tissue sample are rearranged and have precisely the same length, implying that they are derived from the same unique molecule.

Present methods for detection of monoclonality are based on restriction enzyme digestion, followed by Southern blotting and gene probing. This approach is complex, expensive and time consuming, so that information is usually provided too late to be of substantial practical value.

By contrast, the method of the present invention provides a rapid and sensitive diagnostic test. In addition, it is also very versatile as material which can be used as the tissue sample includes blood, turnout tissue in node or bone marrow, formalin-fixed embedded histological material, aspirated cytological material or cells on slides.

According to the present invention, there is provided a method for lymphoid leukaemia and/or lymphoma in a tissue sample, which comprises the determination of the homogeneity or heterogeneity of the length of immunoglobulin and/or T-receptor gene segments in said tissue sample to indicate the presence or absence of monoclonality of the B- and/or T-lymphocyte population in said sample.

According to one embodiment of the present invention there is provided a method for the detection of monoclonality and presumptive malignancy in a tissue sample, and/or for the determination of the B-lymphocyte or T-lymphocyte origin of a tumour, which comprises the steps of:

(a) amplification of immunoglobulin and/or T-receptor gene segments in said tissue sample by means of the polymerase chain reaction using specific primers or mixtures of primers for said immunoglobulin and/or T-receptor gene segments; and
(b) size separation of the amplified segments to determine homogeneity or heterogeneity of the length of the amplified segments.

In one particular embodiment, the primers used are consensus primers for the immunoglobulin and/or T-receptor gene segments.

The present invention also extends to a kit for performance of the method of the invention as broadly outlined above, comprising a set of specific primers or mixtures of primers for immunoglobulin and/or T-receptor gene segments for amplification of immunoglobulin and/or T-receptor gene segments in a tissue sample by the polymerase chain reaction.

Once again, in a particular embodiment, the primers used are consensus primers for the immunoglobulin and/or T-receptor gene segments.

The immunoglobulin (Ig) and T-receptor (Tr) genes are present in all cells. Each consists of 4 families, the variable (V), diversity (D), joining (J), and constant (C) region family (except for immunoglobulin light chains which lack a D segment). In the process of development of a B- or T-lymphocyte, the gene is rearranged so that one randomly chosen member of each family is joined together to form the final molecule. Random mutations also occur at the VD, DJ and JC joining points. As a result of this random joining and mutation, the final immunoglobulin or T-receptor molecule is virtually unique. However, there are two features of particular importance with regard to the present invention:

(a) The number of bases removed and/or inserted at the VD, DJ and JC junctions is quite variable, so that different immunoglobulin or T-receptor molecules, particularly the segments spanning VD, DJ and JC junctions, differ substantially in length.
(b) There are some regions of similarity if not of absolute identity within the genes. These comprise regions, and parts of the J and C regions.

The present invention involves the use of the polymerase chain reaction (PCR) in a new way. The PCR is now well known, having been first described in 1985, and it enables the exponential amplification of small cDNA segments provided that their sequence is known. The principle of the PCR is that two DNA primers, one for each DNA strand, are used in successive cycles of denaturation followed by DNA synthesis and this results in exponential amplification of the segment of DNA bounded by the primers. As each cycle takes 6–7 minutes, it is practical to perform 20-30 cycles, and as each cycle may be up to 70-80% efficient, there can be amplification of up to $10^6$-fold at high fidelity.

The PCR as described is based on primers, each exactly complementary to a known sequence. In one embodiment of the present invention, the problem of amplifying immunoglobulin and T-receptor molecules has been solved by utilizing consensus primers to regions which have a similar but not identical sequence in the immunoglobulin and T-receptor genes respectively. These regions comprise the framework portions of the V regions of the immunoglobulins, conserved V regions of the T-receptor genes, and parts of the D,J and/or C regions of the immunoglobulin or T-receptor genes.

size separated molecules can be identified by non-isotopic means, e.g. ethidium bromide staining, by radioisotope incorporation, or by Southern transfer and hybridization to an internal probe.

Further features of the present invention will be apparent from the following detailed description.

A. SYNTHESIS OF PRIMERS

1. Primers for the Immunoglobulin Gene The 4 regions of DNA sequence which are similar in all immunoglobulin heavy chain genes are:

(a) in the 3' end of the J-region, 30 of 34 bases are conserved in all six germ-line J-chains. 3 DNA primers which will stick to the (+) strand DNA have been used:

| | | | |
|---|---|---|---|
| ELJ$_H$-5' | TGAGG AGACG | GTGAC CAGGG | TNCCT TGGCC CCAG3' |
| LJ$_H$- 5' | TGAGG AGACG | GTGAC C | 3' |
| VLJ$_H$-5' | | GTGAC CAGGG | TNCCT TGGCC CCAG3' |

Primers to these regions work for two reasons. Firstly, they have a structure which is sufficiently homologous to the appropriate region of the immunoglobulin or T-receptor DN; or RNA to recognise only those regions in total DNA or RNA. Secondly, the PCR region will only work if the sequence recognised by the two primers is short. This condition only obtains for those segments of DNA or RNA in which the V, D and J (or C) regions have been joined together and a mature immunoglobulin or T-receptor molecule has been formed. As a result of these two properties, the primers will recognise and amplify only the final mature immunoglobulin or T-receptor molecule.

Use of these primers in the PCR will result in amplification of the inter-primer segments of all mature immunoglobulin or T-receptor molecules in a tissue sample. The amplified segments will cross the VD, DJ (and JC) junctions. As a result the final amplified piece of DNA, irrespective of its sequence, will have a single length if all of the immunoglobulin or T-receptor genes in the tissue are derived from a monoclonal, malignant population or will have a heterogenous length if the molecules are derived from a heterogenous non-malignant population. Primers for the immunoglobulin molecule will identify malignant populations of B-lymphocyte origin, primers for the T-receptor molecule will identify malignancy of T-lymphocyte origin.

The lengths of the amplified pieces of DNA can be simply determined by separating the DNA molecules by a technique which separates molecules on the basis of size. At present electrophoresis in agarose or polyacrylamide gel is used but chromatography would have advantages owing to the feasibility of automation. The (wherein N represents any of the four nucleotide bases.)

(b)–(d) the v-region can be subdivided into 3 "framework" regions and intervening "chain determining" regions. The "framework" regions are similar in all immunoglobulins; the "chain determining" regions vary greatly. By comparing sequence of 17 lymphocyte lines, conserved stretches of DNA have been identified in each framework region. However, the sequences are not highly conserved. As it is not clear how mis-match will affect the PCR, redundancies have been introduced into some synthetic primers. Primers which will hybridize to (−) strand of DNA include:

| | | | | |
|---|---|---|---|---|
| FR1BR: | 5' CT[C/G][T/A]C | CTG[T/C][G/A] | CAG[T/C]C | TCTGG 3' |
| FR1BS: | 5' CTCTC | CTGTG | CAGCC | TCTGG 3' |
| FR2A: | 5' TGG[A/G]T | CCG[C/A]C | AG[G/C]C[T/C] | [T/C]CNGG 3' |
| 5FR3A: | 5' ACACG | GC[C/T][G/C]T | GTATT | ACTGT 3' |

Primers which stick to the (+) strand of DNA include:

| | | | | |
|---|---|---|---|---|
| FR3A-: | 5' ACAGT | AATAC | A[G/C][A/G]GC | CGTGT 3' |

Primers which stick to the opposite strand of DNA and/or for the other immunoglobulin chains could equally well be used.

Primers modified to contain internal or terminal restriction enzyme sites have also been used successfully. They aid subsequent cloning.

2. Primers for the T-receptor Gene

Analogous primers are used for the T-receptor genes. The principles applied in selecting primers for these genes are the same as for the immunoglobulin gene but there are some differences of emphasis. In particular, there is more emphasis on generation of diversity by removal of nucleotides and insertion of random nucleotides at VD, DJ and JC junctions. The V-regions of the T-receptor cannot be divided easily into less variable and "framework" and more variable "chain determining" regions. However, near the VD junction a stretch of about 20 bases is conserved.

(a) T-receptor alpha chain

| | |
|---|---|
| JAT1 | 5' TTC CAA AGA TCA G(T/C)T TG 3' |
| JAT2 | 5' A(A/G)C CTG GT(T/C) CCT (T/G)(T/G)T CAA A3' |
| 3VTA | 5' GA(C/T) TCA GC (T/C) GTG TAC (T/C) (T/A) (C/T) TG 3' |
| 5VTA1 | 5' (A/T)AC (C/T)T(A/C) (C/T)TC TGG TA(C/T) AA(A/G) CA 3' |
| CTA | 5' GAA TAG GCA GAC AGA CTT GT 3' |

-continued

| | |
|---|---|
| PTA | 5' ACT GGA TTT AGA GTC TCT 3' |

JAT2 is the J-region primer for the PCR.
JAT1 is an internal probe.
3VTA is the V-region primer for the PCR, about 80 base pairs from JAT1.
5VTA is a V-region primer 200-300 base pairs from JAT1.
CTA and PTA are within the constant region.
The v-and J-region primers are consensus primers.
(b) T-receptor beta chain

| | |
|---|---|
| JBT1 | 5' CG GGT (G/C)CC T(T/G)G CCC (G/A)AA 3' |
| JBT2 | 5' AG CAC GGT GAG CC(G/T) (G/T)GT (G/C)CC 3' |
| 3VTB1 | 5' GAC (T/A)(C/G)A (G/A)(G/C)C GTG TAT CT(C/T) TG3' |
| 3VTB2 | 5' CAG ACA TCT CTG TAC (C/T)TC TGT GCC 3' |
| 5VTB1 | 5' C(A/T)(C/A)(T/C)(A/C) T (T/G)T(A/T)(T/C) TGGTA CCGAC AG 3' |
| 5VTB2 | 5' TGTAC TGGTA TCGAC AAG 3' |
| CTB | 5' TTT GGG TGT GGG AGA TCT CTG C 3' |
| PTB | 5' CTT CTG ATG GCT CAA ACA 3' |

JBT2 is a J-region primer for the PCR.
JBT1 is an internal probe.
3VTB1 and 3VTB2 are V-region primers about 80 base pairs from JBT1, for TCR beta subclasses Beta$_1$ and Beta$_2$ respectively.
5VTB1 and 5VTB2 are V-region primers 200-300 base pairs from JBT1, for TCR beta subclasses Beta$_1$ and Beta$_2$ respectively.
CTB and PTB are within the constant region for all Beta genes.
The V- and J-region primers are consensus primers.
(c) T-receptor gamma chain

| | |
|---|---|
| JGT12- | 5' AAG TGT TGT TCC ACT GCC AAA 3' |
| 3VTG | 5' GTC TAT TAC TGT GCC ACC TGG 3' |
| CTG | 5' TCT GGA GCT TTG TTT CAG CAA 3' |
| PTG | 5' GGA AGA AAA ATA GTG GGC 3' |

JGT12 is a J-region primer for the PCR. It is based on the sequence of two of the four known J-chains of TCR class Gamma.
3VTG is a V-region primer about 80 base pairs from JGT12.

CTG and PTG are within the constant region.
As constant region primers are sometimes used for amplification, depending on the individual case, it may be necessary to precede the PCR amplification by starting from RNA and carrying out one round of reverse transcription.

The internal probes JAT1 and JBT1 described above can be used for final detection of an amplified product if it cannot be visualized as an ethidium-stained band. The probe can be labelled, usually radioactively, and thereby provides a very sensitive and specific method for detection of the amplified product.

An alternative approach applicable to the gamma chain (Tg receptor) is to use a mixture of primers for the 9 V-regions and 5 J-regions. Sequences used are:

| Primer | Sequence |
|---|---|
| | V-regions |
| TCRVG2PST | 5' CTTC CTGCAG ATG ACT CCT ACA ACT CCA AGG TTG 3' |
| TCRVG3PST | 5' CTTC CTG CAG ATG ACG TCT CCA CCG CAA GGG ATG 3' |
| TCRVG4PST | 5' CTTC CTG CAG ATG ACT CCT ACA CCT CCA GCG TTG 3' |
| TCRVG5PST | 5'TTC CTG CAG ATG ACG TCT CCAA CTC AAA GGA TG 3' |
| TCRVG8PST | 5' CTTC CTGCAG ATG ACT CCT ACA ACT CCA GGG TTC 3' |
| TCRVG9PST | 5' GG(A/G/C/T) ACTG CAG GAA AG GAA TCTG GCATT CCG 3' |
| TCRVG10PST | 5' CT CTG CAG AAT CCG CAG CTC GAC GCA GCA 3' |
| TCRVG11PST | 5' CA CTG CAG GCT CAA GAT TGC TCA GGT GGG 3' |
| TCRVG12PST | 5' ACT CTG CAG CCT CTT GGG CAC TGC TCT AAA 3' |
| | J-regions |
| JGT$_{12}$- | 5' AAG TGT TGT TCC ACT GCC AAA 3' |
| JGT$_3$ | 5' AGTTA CTA TG AG C (T/C) T AGT CCC 3' |
| JGT$_4$ | 5' TGT AAT GAT AAG CTT TGT TCC 3' |

The V-region primers contain 20-24 bases (those nearest the 3' end) which match the target precisely. They also contain, near the 5' end, the sequence CTGCAG, as site for a restriction enzyme. This site will aid subsequent cloning, should cloning be necessary.

B. AMPLIFICATION OF DNA

Both DNA or RNA may be used. cDNA is made from RNA using reverse transcriptase and one or both PCR primers. The cDNA is precipitated and resuspended in water and the PCR reaction then used. Approximately 30 cycles of the reaction are performed using polymerase from *Thermus aquaticus*. Products of the reaction are separated on agarose gels and become visible following staining with ethidium bromide. Southern blotting and hybridization to a DNA probe which binds internal to the primer binding sites is also usually performed. Control size-markers aid in determining size of the amplified segment.

C. RESULTS OF TESTING FOR MONOCLONALITY USING CONSENSUS IMMUNOGLOBULIN PRIMERS

Tables 1 and 2 set out the results of testing various samples for monoclonality using the immunoglobulin gene only.

TABLE 1

Results on Extracted DNA

| Material | Number | Result |
|---|---|---|
| Normal T cell clones | 15 | no amplification |
| Comment: As predicted. | | |
| Normal B cell clones | 16 | 1 or 2 discrete bands |
| Comment: As predicted. | | |
| Normal mixed blood lymphocytes | 20 | diffuse peak |
| Comment: As predicted. | | |
| B-cell lymphomas | 24 | 1 or 2 discrete bands in 19*, no amplification in 5** |

Comment: *As predicted. **The cases showing no amplification probably represent cases with an unusual form of rearrangement.

TABLE 2

Results on Fixed Material and Node Aspirates

| Material | Number | Results |
|---|---|---|
| Fixed material | | |
| B cell lymphomas | 26 | 1 or 2 discrete bands in 24. |
| T cell lymphomas | 7 | no amplification |
| Reactive nodes | 9 | no amplification |
| Carcinomas | 12 | no amplification |
| Node aspirates | | |
| B cell lymphomas | 5 | 1 or 2 discrete bands in 3 |
| Carcinomas | 2 | no amplification. |

These results were obtained using primers $LJ_H^-$ and FR3A described above. Thirty cycles of amplification were performed and the amplified fragments were electrophoresed in 2% agar and stained with ethidium bromide to enable visualisation with ultraviolet light. Similar results have been obtained by adding radioactive nucleotide (CTP) for the last five cycles of amplification, electrophoresing, and visualising the fragments by autoradiography.

D. RESULTS OF TESTING FOR MONOCLONALITY USING T-RECEPTOR PRIMERS.

Using the same PCR procedures as described above with one or other pairs of consensus primers, a discrete rearrangement has been detected using one or other pair of primers in 6 of 8 normal T-cell clones.

TABLE 3

Results on 8 normal T-cell clones using consensus primers.

| Primer combination | Number of clones showing a discrete band |
|---|---|
| 3VTA & JAT2 | 3 |
| 3VTA & JBT2 | 5 |
| 3VTB2 & JBT2 | 2 |
| 5VTB1 & JBT1 | 5 |
| 5VTB2 & JBT2 | 4 |

Similarly, using a mixture of all 9 V-region primers as previously described (TCRVG2PST-TCRVG12PST, and $JGT_{12}$-, $JGT_3$ and $JGT_4$) a discrete rearrangement has been detected in 3 of 4 normal T-cell clones.

We claim:

1. A method for the detection of B-cell lymphoid leukemia or B-cell lymphoma in a tissue sample which comprises determining the homogeneity or heterogeneity of the length of immunoglobulin gene segments resulting from immunoglobulin gene rearrangements in said tissue sample, wherein homogeneity is indicative of B-cell lymphoid leukemia or B-cell lymphoma.

2. A method for the detection of T-cell lymphoid leukemia or T-cell lymphoma in a tissue sample, which comprises determining the homogeneity or heterogeneity of the length of T-receptor gene segments resulting from T-receptor gene rearrangements in said tissue sample, wherein homogeneity is indicative of T-cell lymphoid leukemia or T-cell lymphoma.

3. A method for determining the B-cell or T-cell origin of a lymphoid leukemia or lymphoma in a tissue sample, which comprises determining the homogeneity or heterogeneity of the length of immunoglobulin gene segments resulting from immunoglobulin gene rearrangements and T-receptor gene segments resulting from T-receptor gene rearrangements in said tissue sample, wherein homogeneity of immunoglobulin gene segments is indicative of B-cell origin of a lymphoid leukemia or lymphoma and homogeneity of T-receptor gene segments is indicative of T-cell origin of a lymphoid leukemia or lymphoma.

4. The method of claim 1 wherein determining said homogeneity or said heterogeneity comprises:
   (a) amplifying said immunoglobulin gene segments in said tissue sample by the polymerase chain reaction using at least one pair of primers specific for said immunoglobulin gene segments;
   (b) separating said amplified immunoglobulin gene segments by size; and
   (c) detecting said size-separated amplified immunoglobulin gene fragments.

5. The method of claim 2 wherein determining said homogeneity or said heterogeneity comprises:
   (a) amplifying said T-receptor gene segments in said tissue sample by the polymerase chain reaction using at least one pair of primers specific for said T-receptor gene segments;
   (b) separating said amplified T-receptor gene segments by size; and
   (c) detecting said size-separated amplified T-receptor gene fragments.

6. The method according to claim 3 wherein determining said homogeneity or said heterogeneity of said immunoglobulin gene segments and said T-receptor gene segments comprises:
   (a) amplifying said immunoglobulin and T-receptor gene segments in said tissue sample by the polymerase chain reaction using at least one pair of primers specific for said immunoglobulin gene segment and at least one pair of primers specific for said T-receptor gene segments;
   (b) separating said amplified immunoglobulin and T-receptor gene segments by size; and
   (c) detecting said size-separated amplified immunoglobulin and T-receptor gene fragments.

7. The method of claim 4 wherein said immunoglobulin gene segments comprise at least one of a V-D, D-J and V-J junction.

8. The method of claim 5 wherein said T-receptor gene segments comprise at least one of a V-D, D-J and V-J junction.

9. The method of claim 6 wherein said immunoglobulin gene segments comprise at least one of a V-D, D-J and V-J junction and wherein said T-receptor gene segments comprise at least one of a V-D, D-J and V-J junction.

10. The method of any one of claims 4–6 and 1–3 wherein said tissue sample is blood, tumor tissue in node or bone marrow, formalin-fixed embedded histological material, aspirated cytological material or cells on slides.

11. The method of any one of claims 4–6 wherein said separating is accomplished by electrophoresis or chromatography.

12. The method of claim 11 wherein said electrophoresis is agarose or polyacrylamide gel electrophoresis.

13. The method of any one of claims 4–6 wherein said detection is accomplished by non-isotopic means, radio-isotope incorporation, or Southern transfer and hybridization to an internal probe.

14. The method according to claim 13 wherein said detection by non-isotopic means comprises ethidium bromide staining.

15. The method of claim 4 or 6 wherein said primers specific for said immunoglobulin gene segments are selected from primers to the framework portion of the V regions, primers to parts of the D region, primers to parts of the J region, and primers to parts of the C region of the immunoglobulin gene.

16. The method of claim 5 or 6 wherein said primers for T-receptor gene segments are selected from primers to the conserved V regions, primers to parts of the D region, primers to parts of the J regions and primers to parts of the C region of the T-receptor gene.

17. The method of claim 4 or 6 wherein said primers specific for said immunoglobulin gene segment are consensus primers for the immunoglobulin gene segment.

18. The method of claim 4 or 6 wherein one of said pair of primers specific for said immunoglobulin gene segments is a primer to the V region of the immunoglobulin gene and the other of said primers is a primer to the J region of the immunoglobulin gene.

19. The method of claim 18 wherein said primer to the V region of the immunoglobulin gene is FR3A and said primer to the J region of the immunoglobulin gene is $LJ_H^-$.

20. The method of claim 5 or 6 wherein said primers specific for said T-receptor gene segment are consensus primers for the T-receptor gene segment.

21. The method of claim 5 or 6 wherein one of said pair of primers specific for said T-receptor gene segments is a primer to the V region of the T-receptor gene and the other of said primers is a primer to the J region of the T-receptor gene.

22. The method of claim 4 or 6 wherein one of said pair of primers specific for said immunoglobulin gene segment is selected from the group consisting of:

| | |
|---|---|
| $ELJ_H^-$: | 5' TGAGGAGACGGTGACCAGGGTNCCTTGGCCCCAG 3'; |
| $LJ_H^-$: | 5' TGAGGAGACGGTGACC 3'; and |
| $VLJ_H^-$: | 5' GTGACCAGGGTNCCTTGGCCCCAG 3', | and the other of said primers is selected from the group consisting of:

| | |
|---|---|
| FR1BR: | 5' CT[C/G][T/A]CCTG[T/C][G/A]CAG[T/C]C TCTGG 3'; |
| FR1BS: | 5' CTCTCCTGTGCAGCCTCTGG 3'; |
| FR2A: | 5' TGG[A/G]TCCG[C/A]CAG[G/C]C[T/C][T/C]CNGG 3'; |
| FR3A: | 5' ACACGGC[C/T][G/C]TGTATTACTGT 3'; and |
| FR3A-: | 5' ACAGTAATACA[G/C][A/G]GCCGTGT 3' | wherein N represents any nucleotide base.

23. The method of claim 5 or 6 wherein said primers specific for said T-receptor gene segment are selected from the group consisting of:

| | |
|---|---|
| JAT1: | 5' TTCCAAAGATCAG(T/C)TTG 3'; |
| JAT2: | 5' A(A/G)CCTGGT(T/C)CCT(T/G)(T/G)TCAAA 3'; |
| 3VTA: | 5' GA(C/T)TCAGC(T/C)GTGTAC(T/C)(T/A)(C/T)TG 3'; |
| 5VTA1: | 5' (A/T)AC(C/T)T(A/C)(C/T)TCTGGTA(C/T)AA(A/G)CA 3'; |
| CTA: | 5' GAATAGGCAGACAGACTTGT 3'; |
| PTA: | 5' ACTGGATTTAGAGTCTCT 3'; |
| JBT1: | 5' CGGGT(G/C)CCT(T/G)GCCC(G/A)AA 3'; |
| JBT2: | 5' AGCACGGTGAGCC(G/T)(G/T)GT(G/C)CC 3'; |
| 3VTB1: | 5' GAC(T/A)(C/G)A(G/A)(G/C)CGTGTATCT(C/T)TG 3'; |
| 3VTB2: | 5' CAGACATCTCTGTAC(C/T)TCTGTGCC 3'; |
| 5VTB1: | 5' C(A/T)(C/A)(G/C)(A/C)T(T/G)T(A/T)(T/C)TGGTACCG ACAG 3'; |
| CTB: | 5' TTTGGGTGTGGGAGATCTCTGC 3'; |
| PTB: | 5' CTTCTGATGGCTCAAACA 3'; |
| JGT12: | 5' AAGTGTTGTTCCACTGCCAAA 3'; |
| 3VTG: | 5' GTCTATTACTGTGCCACCTGG 3'; |
| CTG: | 5' TCTGGAGCTTTGTTTCAGCAA 3'; and |
| PTG: | 5' GGAAGAAAAATAGTGGGC 3'. |

24. The method of claim 5 or 6 wherein one of said pair of primers specific for said T-receptor gene segment is selected from the group consisting of:

| | |
|---|---|
| TCRVG2PST | 5' CTTCCTGCAGATGACTCCTACAACTCCAAGGTTG 3'; |
| TCRVG3PST | 5' CTTCCTGCAGATGACGTCTCCACCGCAAGGGATG 3'; |
| TCRVG4PST | 5' CTTCCTGCAGATGACTCCTACACCTCCAGCGTTG 3'; |

-continued

| | |
|---|---|
| TCRVG5PST | 5' TTCCTGCAGATGACGTCTCCAACTCAAAGGATG 3'; |
| TCRVG8PST | 5' CTTCCTGCAGATGACTCCTACAACTCCAGGGTTC 3'; |
| TCRVG9PST | 5' GG(A/G/C/T)ACTGCAGGAAAGGAATCTGGCATTCCG 3'; |
| TC4VG10PST | 5' CTCTGCAGAATCCGCAGCTCGACGCAGCA 3'; |
| TC4VG11PST | 5' CACTGCAGGCTCAAGATTGCTCAGGTGGG 3'; and |
| TCRVG12PST | 5' ACTCTGCAGCCTCTTGGGCACTGCTCTAAA 3' | and the other of said pair of primers specific for said T-receptor gene segment is selected from the group consisting of:

| | |
|---|---|
| JGT$_{12}$: | 5' AAGTGTTGTTCCACTGCCAAA 3'; |
| JGT$_3$: | 5' AGTTACTATGAGC(T/C)TAGTCCC 3'; and |
| JGT$_4$: | 5' TGTAATGATAAGCTTTGTTCC 3'. |

25. A kit for the detection of lymphoid leukemia or lymphoma comprising a first container containing at least one pair of primers specific for immunoglobulin gene segments resulting from immunoglobulin gene rearrangement, and a second container containing reagents for a polymerase chain reaction.

26. The kit of claim 25 wherein one of said pair of primers is selected from the group consisting of:

| | |
|---|---|
| ELJ$_H^-$: | 5' TGAGGAGACGGTGACCAGGGTNCCTTGGCCCCAG 3'; |
| LJ$_H^-$: | 5' TGAGGAGACGGTGACC 3'; and |
| VLJ$_H^-$: | 5' GTGACCAGGGTNCCTTGGCCCCAG 3', | and the other of said primers is selected from the group consisting of:

| | |
|---|---|
| FR1BR: | 5' CT[C/G][T/A]CCTG[T/C][G/A]CAG[T/C]C TCTGG 3'; |
| FR1BS: | 5' CTCTCCTGTGCAGCCTCTGG 3'; |
| FR2A: | 5' TGG[A/G]TCCG[C/A]CAG[G/C]C[T/C][T/C]CNGG 3'; |
| FR3A: | 5' ACACGGC[C/T][G/C]TGTATTACTGT 3'; and |
| FR3A-: | 5' ACAGTAATACA[G/C][A/G]GCCGTGT 3' | wherein N represents any nucleotide base.

27. A kit for the detection of lymphoid leukemia or lymphoma comprising a first container containing at least one pair of primers specific for T-receptor gene segments resulting from T-receptor gene rearrangement, and a second container containing reagents for a polymerase chain reaction.

28. The kit of claim 27 wherein one of said pair of primers is selected from the group consisting of

| | |
|---|---|
| TCRVG2PST | 5' CTTCCTGCAGATGACTCCTACAACTCCAAGGTTG 3'; |
| TCRVG3PST | 5' CTTCCTGCAGATGACGTCTCCACCGCAAGGGATG 3'; |
| TCRVG4PST | 5' CTTCCTGCAGATGACTCCTACACCTCCAGCGTTG 3'; |
| TCRVG5PST | 5' TTCCTGCAGATGACGTCTCCAACTCAAAGGATG 3'; |
| TCRVG8PST | 5' CTTCCTGCAGATGACTCCTACAACTCCAGGGTTC 3'; |
| TCRVG9PST | 5' GG(A/G/C/T)ACTGCAGGAAAGGAATCTGGCATTCCG 3'; |
| TC4VG10PST | 5' CTCTGCAGAATCCGCAGCTCGACGCAGCA 3'; |
| TC4VG11PST | 5' CACTGCAGGCTCAAGATTGCTCAGGTGGG 3'; and |
| TCRVG12PST | 5' ACTCTGCAGCCTCTTGGGCACTGCTCTAAA 3', | and the other of said pair of primers is selected from the group consisting of:

| | |
|---|---|
| JGT$_{12}$: | 5' AAGTGTTGTTCCACTGCCAAA 3'; |
| JGT$_3$: | 5' AGTTACTATGAGC(T/C)TAGTCCC 3'; and |
| JGT$_4$: | 5' TGTAATGATAAGCTTTGTTCC 3'. |

29. A kit for the detection of lymphoid leukemia or lymphoma comprising a first container containing at least one pair of primers specific for immunoglobulin gene segments resulting from immunoglubulin gene rearrangement and at least one pair of primers specific for T-receptor gene segments resulting from T-receptor gene rearrangement, and a second container containing reagents for a polymerase chain reaction.

30. The kit of claim 25 or 29 wherein one of said pair of primers specific for said immunoglobulin gene segment is a primer to the V region of the immunoglobulin gene and the second of said pair of primers is a primer to the J region of the immunoglobulin gene.

31. The kit of claim 30 wherein said primer to the V region of the immunoglobulin gene is FR3A and said primer to the J region of the immunoglobulin gene is LJ$_H^-$.

32. The kit of claim 27 or 29 wherein one of said pair of primers specific for said T-receptor gene segment is a primer to the V region of the T-receptor gene and the second of said pair of primers is a primer to the J region of the T-receptor gene.

33. The kit of claim 29 wherein one of said primers specific for said immunoglobulin gene segment is selected from the group consisting of:

| | |
|---|---|
| ELJ$_H^-$: | 5' TGAGGAGACGGTGACCAGGGTNCCTTGGCCCCAG 3'; |
| LJ$_H^-$: | 5' TGAGGAGACGGTGACC 3'; and |

-continued

| | |
|---|---|
| VLJ$_H^-$: | 5' GTGACCAGGGTNCCTTGGCCCCAG 3', | and the other of said primers specific for said immunoglobulin gene segment is selected from the group consisting of:

| | |
|---|---|
| FR1BR: | 5' CT[C/G][T/A]CCTG[T/C][G/A]CAG[T/C]C TCTGG 3'; |
| FR1BS: | 5' CTCTCCTGTGCAGCCTCTGG 3'; |
| FR2A: | 5' TGG[A/G]TCCG[C/A]CAG[G/C]C[T/C][T/C]CNGG 3'; |
| FR3A: | 5' ACACGGC[C/T][G/C]TGTATTACTGT 3'; and |
| FR3A-: | 5' ACAGTAATACA[G/C][A/G]GCCGTGT 3' | and one of said primers specific for said T-receptor gene segments is selected from the group consisting of:

| | |
|---|---|
| TCRVG2PST | 5' CTTCCTGCAGATGACTCCTACAACTCCAAGGTTG 3'; |
| TCRVG3PST | 5' CTTCCTGCAGATGACGTCTCCACCGCAAGGGATG 3'; |
| TCRVG4PST | 5' CTTCCTGCAGATGACTCCTACACCTCCAGCGTTG 3'; |
| TCRVG5PST | 5' TTCCTGCAGATGACGTCTCCAACTCAAAGGATG 3'; |
| TCRVG8PST | 5' CTTCCTGCAGATGACTCCTACAACTCCAGGGTTC 3'; |
| TCRVG9PST | 5' GG(A/G/C/T)ACTGCAGGAAAGGAATCTGGCATTCCG 3'; |
| TC4VG10PST | 5' CTCTGCAGAATCCGCAGCTCGACGCAGCA 3'; |
| TC4VG11PST | 5' CACTGCAGGCTCAAGATTGCTCAGGTGGG 3'; and |
| TCRVG12PST | 5' ACTCTGCAGCCTCTTGGGCACTGCTCTAAA 3', | and the other of said primers specific for said T-receptor gene segment is selected from the group consisting of:

| | |
|---|---|
| JGT$_{12}$: | 5' AAGTGTTGTTCCACTGCCAAA 3'; |
| JGT$_3$: | 5' AGTTACTATGAGC(T/C)TAGTCCC 3'; and |
| JGT$_4$: | 5' TGTAATGATAAGCTTTGTTCC 3'. |

* * * * *

UNITED STATES PATENT AND TRADEMARK OFFICE
CERTIFICATE OF CORRECTION

PATENT NO. : 5,418,134
DATED : May 23, 1995
INVENTOR(S) : Alexander A. Morley, et al.

It is certified that error appears in the above-indentified patent and that said Letters Patent is hereby corrected as shown below:

Column 1, lines 44-45 & 67: "turnout" should read --tumour--

Column 2, line 57: after "comprise" insert --certain parts of the V regions, termed "framework"--

Column 3, line 24: "DN" should read --DNA--

Column 6, line 39: "S'TTC" should read --5'TTC--

Column 12, line 18, Claim 29: "immunoglubulin" should read --immunoglobulin--

Signed and Sealed this

Twenty-third Day of April, 1996

Attest:

BRUCE LEHMAN

*Attesting Officer*  *Commissioner of Patents and Trademarks*